United States Patent [19]

Login et al.

[11] Patent Number: 4,952,559

[45] Date of Patent: * Aug. 28, 1990

[54] FRAGRANCE ADDITIVE

[75] Inventors: Robert B. Login, Oakland; Michael W. Helioff, Westfield, both of N.J.

[73] Assignee: GAF Chemicals Corporation, Wayne, N.J.

[*] Notice: The portion of the term of this patent subsequent to Feb. 28, 2006 has been disclaimed.

[21] Appl. No.: 317,394

[22] Filed: Mar. 1, 1989

Related U.S. Application Data

[63] Continuation-in-part of Ser. No. 922,923, Oct. 24, 1986, Pat. No. 4,732,990, and a continuation-in-part of Ser. No. 91,010, Aug. 28, 1987, Pat. No. 4,883,655, and a continuation-in-part of Ser. No. 91,008, Aug. 28, 1987, Pat. No. 4,830,858, and a continuation-in-part of Ser. No. 91,149, Aug. 28, 1987, Pat. No. 4,837,013, and a continuation-in-part of Ser. No. 67,195, Jun. 29, 1987, Pat. No. 4,834,970.

[51] Int. Cl.$^5$ .............................................. A61K 7/46
[52] U.S. Cl. .......................................... 512/10; 512/3; 512/2
[58] Field of Search ................................. 512/10, 3, 2

[56] References Cited

U.S. PATENT DOCUMENTS

| | | | |
|---|---|---|---|
| 2,786,834 | 3/1957 | Rice et al. | 512/10 X |
| 3,687,692 | 8/1972 | Pittet et al. | 512/10 X |
| 3,782,973 | 1/1974 | Pittet et al. | 512/10 X |
| 4,732,990 | 3/1988 | Login et al. | 546/243 X |
| 4,808,569 | 2/1989 | Chaudhuri et al. | 512/3 X |
| 4,830,850 | 5/1989 | Login et al. | 424/70 |
| 4,830,851 | 5/1989 | Tracy et al. | 546/243 X |
| 4,834,970 | 5/1989 | Login et al. | 424/70 |
| 4,837,013 | 6/1989 | Login et al. | 424/70 |

Primary Examiner—Joseph Paul Brust
Attorney, Agent, or Firm—Marilyn J. Maue; Joshua J. Ward

[57] ABSTRACT

The invention relates to an odoriferous formulation containing an odoriferous compound of between 3 and 60 carbon atoms and having an acidic hydrogen atom and a quaternized fragrance extender having the formula

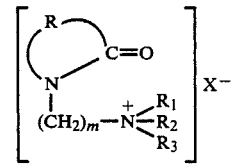

wherein $X^-$ is an anion; m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxyalkyl, alkoxy, alkyleneoxyalkenyl, alkylhydroxy, aryl, aralkenyl, aralkyl, alkaryl, alkyleneamidoalkyl, alkylenecarbamoylkyl, arylenecarbamoylalkyl and aryleneamidoalkyl radicals, said groups each having up to 30 carbon atoms and at least one of $R_1$, $R_2$ and $R_3$ is a radical having from 8 to 30 carbon atoms, except that alternatively $R_2$ and $R_3$ with the quaternized nitrogen can form a 5 to 14 membered heterocyclic ring having from 1 to 2 heteroatoms selected from the group of oxygen, nitrogen and sulfur, in which case $R_1$ can be any of the aforementioned groups or can represent a bond in an unsaturated quaternized heterocyclic ring.

23 Claims, No Drawings

FRAGRANCE ADDITIVE

In one aspect, the invention relates to a novel fragrance additive and to the complexed compound formed by its addition to a fragrance bearing compound as well as to the uses of such complexed products.

In another aspect, the invention relates to compositions containing said complexed products.

BACKGROUND OF THE INVENTION

Fragrances for perfumery, cosmetics, detergents and in other commercial products are well known and have long been used to enhance, mask or heighten natural odors of various products or to provide a pleasing scent to the skin, hair or clothing. However, the scents and odors imparted by many of these fragrances are ephemeral, dissipating within a few hours. This is particularly true of aerosol sprays used for colognes, perfume and other cosmetic applications to the hair and skin where, because of the pressure and rapid evaporation of the propellant, many of the top notes and middle notes of the desired scent disappear rapidly and the end note emerges without the complementary benefit of the top and middle components.

Also, fragrances added to commercial formulations, particularly those containing strongly acid or basic components, tend to interact causing alteration of the scent desired, in some cases causing an unpleasant odor and discoloration.

Accordingly, it is an object of this invention to overcome the above deficiencies by means of an economical additive which can be produced by a commercially feasible and inexpensive process.

Another object is to prevent or minimize degradation of pleasing odors and to preserve the top and middle notes of a fragrance formulation.

Another object of this invention is to provide a fragrance component which is capable of masking unpleasant odors with a perfume formulation.

Another object is to heighten the natural odor of a substance.

Still another object is to lower the vapor pressure of a fragrance and extend its odoriferous emanation.

Yet another object is to stabilize fragrance compositions against chemical interaction in commercial formulations and to repress tendencies of discoloration.

THE INVENTION

In accordance with this invention there is provided a lactone fragrance additive having the formula

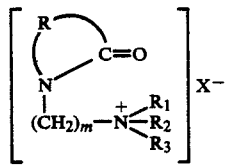

wherein $X^-$ is an anion; m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxyalkyl, alkoxy, alkyleneoxyalkenyl, alkylhydroxy, aryl, aralkenyl, aralkyl, alkaryl, alkyleneamidoalkyl, alkylenecarbamoylalkyl, arylcarbamoylalkyl and arylamidoalkyl radicals, said groups each having from 1 to 30 carbon atoms and at least one of $R_1$, $R_2$ and $R_3$ is a radical having from 8 to 30 carbon atoms, except that $R_2$ and $R_3$ with the quaternized nitrogen can form a 5 to 14 membered heterocyclic ring having from 1 to 2 heteroatoms selected from the group of oxygen, nitrogen and sulfur, in which case $R_1$ can be any of the aforementioned groups or can represent a bond in an unsaturated quaternized heterocyclic ring.

Quaternized fragrance extenders of this invention include all anionic species, particularly organic anionic species of the compounds disclosed in aforementioned copending patent applications of which this application is a continuation-in-part. Such fragrance additives include subspecies having the formulae.

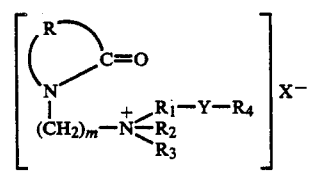

A.

wherein m is an integer having a value of from 1 to 4; R is linear alkylene containing from 3 to 8 carbon atoms and is optionally substituted with lower alkyl; $R_1$ is alkylene containing from 1 to 4 carbon atoms, phenylene or naphthylene optionally substituted with lower alkyl;

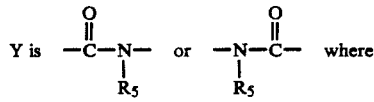

$R_5$ is hydrogen or lower alkyl; $R_4$ is alkyl having from 1 to 30 carbon atoms; $R_2$ and $R_3$ are each independently selected from the group of $-R_1-Y-R_4$, alkyl, alkyleneoxyalkyl, alkylhydroxy, aryl, aralkyl, aralkenyl, alkenylaryl and alkaryl said groups each having from 1 to 30 carbon at ms and at least one of $R_4$, $R_2$ and $R_3$ having 8 or more carbon atoms and $X^-$ is an anion, particularly a chloride, bromide, iodide, lower alkyl tosylate, lower alkyl sulfonate or lower alkyl sulfate anion.

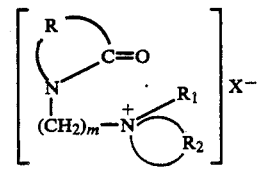

B.

wherein R, $X^-$ and m are as defined in formula A, $R_1$ forms a double bond in the heterocyclic ring with the quaternized nitrogen or is selected from the group consisting of alkyl, hydroxyalkyl, alkyleneoxyalkyl, alkyleneoxy alkenyl, aryl, alkaryl, aralkyl, aralkenyl, alkyleneamidoalkyl, alkylenecarbamoylalkyl, arylcarbamoylalkyl, and arylamidoalkyl and $R_2$, together with the quaternary nitrogen atom forms a 5 to 14 membered heterocyclic structure containing up to 2 hetero atoms, selected from the group of nitrogen, oxygen and sulfur; and

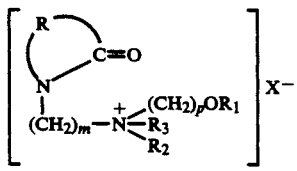

wherein R, X⁻ and m are as defined in formula A; p is an integer having a value of from 1 to 4 and $R_1$ is alkyl or alkenyl having from 1 to 30 carbon atoms and $R_2$ and $R_3$ are each independently selected from the group consisting of —$(CH_2)_pOR_1$, alkyl, hydroxyalkyl, aryl, alkaryl, aralkyl, aralkenyl, alkyleneamidoalkyl, alkylenecarbamoylalkyl, arylcarbamoylalkyl, and arylamidoalkyl radicals, said groups having up to 30 carbon atoms and at least one of $R_1$, $R_2$ and $R_3$ is a radical containing from 8 to 30 carbon atoms.

The above compounds are added to fragances having an acidic hydrogen to form a complex through hydrogen bonding.

Of the above lactam fragrance additives, those of formula A having a pyrrolidonyl or caprolactam ring system and wherein X⁻ is an organic anion, such as, a tosylate, sulfonate or sulfate anion are preferred; although higher membered ring systems such as the 2-azacycloheptanone and 2-azacyclooctanone ring systems also can be suitably employed. The heterocyclic rings of the present lactams can also be substituted with lower alkyl; hence the [(3-methyl-2-pyrrolidonyl)methyl] ammonium salts, [(3-butyl-2-pyrrolidonyl)methyl] ammonium salts, [(3,4-diethyl-2-pyrrolidonyl)methyl] ammonium salts, [3-(2,3-dimethyl-2-piperidonyl) propyl] ammonium salts, and the like are also included within the scope of this invention.

Examples of preferred lactams employed in the present invention include

N-methyl-N-(allyloxybutyl)-N-[(2-pyrrolidonyl)methyl]-N-(3-dodecanamidopropyl) ammonium chloride N,N-dimethyl-N-[(2-pyrrolidonyl)methyl]-N-(3-octadecanamidopropyl) ammonium chloride N,N-dimethyl-N-[(2-pyrrolidonyl)methyl]-N-(3-heptadecanamido propyl) ammonium tosylate N-methyl-N-ethyl-N-[(2-pyrrolidonyl)methyl]-N-(3-octadecanamidopropyl) ammonium bromide N-methyl-N-styryl-N-[(2-pyrrolidonyl)methyl]-N-(3-nonanamido propyl) ammonium methyl sulfonate N-methyl-N-tolyl-N-[(2-pyrrolidonyl)methyl]-N-(3-octadecanamidopropyl) ammonium methyl sulfate N-methyl-N-phenyl-N-[(2-pyrrolidonyl)methyl]-N-(3-hexadecanamidopropyl) ammonium tosylate N-decyl-N-methyl-N-[(2-pyrrolidonyl)methyl]-N-(3-dodecanamidopropyl) ammonium tosylate N-methyl-N-[(2-pyrrolidonyl)methyl]-N,N-di(3-hexadecanamidopropyl) ammonium (1-methyl-2-ethylphenyl) sulfonate N,N-diethyl-N-[(2-pyrrolidonyl)methyl]-N-(4-undecanamidophenyl) ammonium ethyl sulfate N-methyl-N-(2-pyrrolidonyl)methyl]-N,N-bis(3-undecanamidopropyl) ammonium tosylate N-methyl-N-(2-pyrrolidonyl methyl]-N,N-bis(4-undecanamidophenyl) ammonium methyl sulfonate N,N-dimethyl-N-[(2-pyrrolidonyl)methyl]-N-(3-octanamidopropyl) ammonium methyl sulfate N,N-dimethyl-N-[(2-pyrrolidonyl)methyl]-N-(3-dodecanamidopropyl) ammonium bromide N-butyl-N--methyl-N-[(2-pyrrolidonyl)methyl]-N-(3-dodecanamidopropyl) ammonium iodide N-phenyl-N-methyl-N-[(2-pyrrolidonyl)methyl]-N-(4-tetradecan amidobutyl) ammonium tosylate N-benzyl-N-methyl-N-[(2-pyrrolidonyl)methyl]-N-(2-hexadecanamidoethyl) ammonium tosylate N-octadecyl-N-methyl-N-[(2-pyrrolidonyl)methyl]-N-(3-octadecanamidopropyl) ammonium tosylate N,N-dimethyl-N-[(2-pyrrolidonyl)methyl]-N-(3-eicosanamidopropyl) ammonium methyl sulfate N-dodecyl-N-ethyl-N-[(2-pyrrolidonyl)methyl]-N-(4-docosanamidobutyl) ammonium ethyl sulfate N-butyl-N-[(2-pyrrolidonyl)methyl]-N,N-bis(3-decanamidopropyl) ammonium butyl sulfate N-methyl-N-[(2-pyrrolidonyl)methyl]-N,N-bis(2-dodecanamidoethyl) ammonium butyl sulfonate N-methyl-N-[2-pyrrolidonyl)methyl]-N,N-bis(tetradecanamidomethyl) ammonium tosylate N-methyl-N-[(2-pyrrolidonyl)methyl]-N,N-bis(3-hexadecanamido propyl) ammonium (1,3-diethylphenyl) sulfonate N-methyl-N-[(2-pyrrolidonyl)methyl]-N,N-bis(3-octadecanamido propyl) ammonium tosylate N-methyl-N-(2-hydroxyethyl)-N-[(2-pyrrolidonyl)ethyl]-N-(3-dodecanamidopropyl) ammonium tosylate N-ethyl-N-hexadecyl-N-[(2-pyrrolidonyl)methyl]-N-(2-octadecanamidoethyl) ammonium tosylate N,N-bis(2-propyleneoxyethyl)-N-[(2-pyrrolidonyl)methyl]-N-(3-propanamidopropyl) ammonium tosylate N,N-distyryl-N-[(2-pyrrolidonyl)methyl]-N-(3-hexadecanamidopropyl) ammonium tosylate N,N-bis(4-butyleneoxybutyl)-N-[(2-pyrrolidonyl)methyl]-N-(3-eicosanamidopropyl) ammonium tosylate N,N-di(3-propanamidopropyl)-N-[(2-pyrrolidonyl)methyl]-N-(4-tetradecanamidobutyl) ammonium tosylate N,N-ditolyl-N-[(2-pyrrolidonyl)methyl]-N-(3-octadecanamidopropyl) ammonium tosylate N,N-dimethyleneoxypropyl-N-[(2-pyrrolidonyl)methyl]-N(4-decanamidobutyl) ammonium tosylate N,N-di-(3-hydroxyoctyl)-N-[(2-pyrrolidonyl)methyl]-N-(2-hexanamidoethyl) ammonium tosylate N,N-diphenyl-N-[(2-pyrrolidonyl)methyl]-N-(2-decanamidoethyl) ammonium tosylate N-[(2-pyrrolidonyl)methyl]-N,N,N-tris(3-tridecanamidopropyl) ammonium tosylate N-[2-(2-pyrrolidonyl)ethyl]-N,N,N-tris(4-pentadecanamidophenyl) ammonium tosylate N-methyl-N-[(2-pyrrolidonyl)methyl]-N,N-bis(tetradecanamidonaphthyl) ammonium tosylate N-[2-(2-propylcarbamoyl)ethyl]-N,N-dimethyl-N-[(2-pyrrolidonyl)methyl] ammonium methyl sulfate N-[2-(2-octadecylcarbamoyl)ethyl -N,N-dimethyl-N-[(2-pyrrolidonyl)methyl] ammonium tosylate N,N,N-tris[2-(2-octadecylcarbamoyl)ethyl]-N-[(2-pyrrolidonyl) methyl] ammonium tosylate N-[(2-pyrrolidonyl)methyl]-N,N,N-tris-(4-octadecanamidobutyl) ammonium tosylate N-[(2-pyrrolidonyl)methyl]-N,N,N-tris-(3-tridecanamidopropyl) ammonium methyl sulfonate N,N-dibenzyl-N-[(2-pyrrolidonyl)methyl]-N-(6-hexadecanamidohexyl) ammonium tosylate N-[(2-pyrrolidonyl)methyl]-N,N,N-tris(3-heptadecanamidopropyl) ammonium methyl sulfate N,N-ditolyl N-[(4-methyl 2-pyrrolidonyl)methyl]-N-(6-pentadecanamidohexyl) ammonium tosylate N-methyl-N-[(4-butyl-2-pyrrolidonyl)methyl]-N,N-bis(heptadecanamidomethyl) ammonium methyl sulfate N,N-dixylyl-N-[(2-piperidinonyl)methyl]-N-(2-heptadecanamidoethyl) ammonium methyl sulfonate N-decyl N-methyl-N-[(2-pyrrolidonyl)methyl]-N-(3-propanamido propyl) ammonium chloride N-dodecyl-N-methyl-N-[(2-pyrrolidonyl methyl]-N-(4-propanamidobutyl) ammonium methyl sulfonate N-methyl-N-(3-octadecanamidopropyl)-N-[(2-pyrrolidonyl)methyl]-N-(3-tetradecanamidopropyl) ammonium tosylate N-methyl-N-styryl-N-[(2-pyrrolidonyl)methyl]-N-(3-eicosanamidopropyl) ammonium tosylate N-methyl-N-(6-hydroxyhexyl)-N-[(2-pyrrolidonyl)methyl]-N-(4-docosanamidobutyl) ammonium tosylate N-(hydroxybutyl)-N-[(2-azacycloheptanonyl)methyl]-N,N-bis(4-octadecanamidobutyl) ammonium tosylate N-styryl-N-[(2-azacyclodecanonyl)methyl]-N,N-bis(3-tetradecanamidopropyl) ammonium tosylate N-methyl-N-[(2-azacyclononanonyl)methyl]-N,N-bis(6-dodecanamidohexyl) ammonium tosylate and others, and other alkylenecarbamoylalkyl and N-heterocyclic counterparts of the above alkyleneamidoalkyl ammonium salts.

Most preferred of the above lactams are the pyrrolidonyl, piperidonyl and azacycloheptanoyl alkyleneamidoalkyl ammonium tosylates.

The quaternized lactams employed in this invention can be prepared by the processes disclosed in the copending parent applications and in U.S. Pat. No. 4,732,990, filed Oct. 24, 1986, entitled QUATERNIZED NITROGEN CONTAINING COMPOUNDS particularly columns 4 and 5 which disclosures are incorporated herein by reference.

The fragrances or osmophores which form complexes with the above lactams are volatile, odoriferous compounds containing an acidic hydrogen which is combinable with the lactam complex through hydrogen bonding at the carbonyl group. Fragrances of this type contain between 3 and 50 carbon atoms and include hydroxylated compounds, aldehydes, primary and secondary amines, primary and secondary amides, acids, and essential oils used for fragrances and perfumery. They may be synthetic or naturally occurring. The use of synthetically prepared fragrances with the present lactams enables the formulator to emphasize certain notes without interference by natural by-odors which the same fragrance would have were it isolated from the natural product. These synthetics are less expensive to obtain and possess more olfactory uniformity and stability than those made with essential oils, natural extractions and other organic materials which are subject to the vagaries of nature. Such synthetics include terpenes, aldehydes, jasmone, linalool and geraniol. However, natural products are used to provide more richness, subtility and natural character. Natural products include essential oils, spices, flower oils in the form of concretes, absolutes, extracts, etc. The hydroxylated compounds include both aliphatic and aromatic compounds which may be additionally substituted with alkyl, alkoxy, ether, ketone, aralkyl, alkaryl, aldehyde or vinyl groups or any combinations thereof. Among the essential oils of this type are included the oils from bergamot, cedarwood, citrus, geranium, guaiacwood, lemon, neroli, orange, patchoudi, rhondinal, rosemary, tangerine and ylang-ylang oils. Also included are extracts, gums and resins such as benzoin, galbanum, labdanum, maté, melilot, myrrh, frankincense, oakmoss, opopanax, orris, styrax and other balsam resins.

Sweet, herbal or floral fragrances are derived from $C_8$–$C_{11}$ aldehydes, amylcinnamic aldehyde, anesic aldehyde, benzaldehyde, hexylcinnamic aldehyde, methyl nonylacetalaldehyde, linalool, peach aldehyde, and oils from carnation, citrus, gardenia, heliotrope, hyacinth, honeysuckle, jasmin, jonquil, lavendar, lavandin, lilac, lily-of-the-valley, mimosa, acacia, orange, rose, rose oxide, rosemary, violet, etc. Spicy fragrances are obtained from oils and extracts of bisal, bay, birch tar, caraway, cinnamon, cedar leaf, clove, clover, musk, nutmeg, oakmoss, orris root, sage, sweet grass, tuberose, tonka, vanillin, ethyl vanillin, benzyl alcohol, ambrettolide, galaxolide, geraniol, hexadecanolide, indole, albdanum, lemon grass, neroli, narcissus, petigrain resida, and ambergris fixative. Various alcohols, ethers and hydrocarbons which are satisfactory osmophores for this invention include phenyl ethyl alcohol, propanol, butanol, pentanol, dodecanol, ethyl sec-butyl ether, diethoxyethane, pinene, camphene, terpinene and others.

Of the above commercially employed fragrances, the hydroxylated compounds and aldehydes are most readily complexed with the present lactams and the most preferred compounds are those having the formula

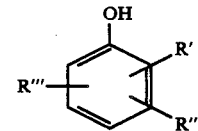

wherein R' is lower alkyl, lower alkoxy, phenyl or lower alkyl ester and R'' and R''' are each independently hydrogen, lower alkyl, lower alkoxy, lower alkenyl, aldehyde, phenyl or lower alkyl ester. Vanillin and ethyl vanillin are examples of this group.

The fragrances of this invention which complex with the present lactams are often employed as perfumery compositions. The following Tables 1-3 are representative examples of such compositions as used in perfumes, creams and soaps.

TABLE 1

| Formulas for Rose Bases, parts by wt. | | | |
|---|---|---|---|
| Ingredients | Perfume | Cream | Soap |
| rhodiol | 50 | 15 | |
| geraniol coeur (perfume grade) | 5 | 15 | 15 |
| citronellol coeur | 10 | 30 | 15 |
| phenylethyl alcohol coeur | 10 | 15 | |
| phenylethyl alcohol white extra | | | 20 |
| nerol coeur | 5 | 5 | |
| geranyl acetate | 2 | 2 | 5 |
| aldehyde C-8, 10% | 4 | 4 | 5 |
| aldehyde C-9, 10% | 4 | 4 | 5 |
| benzophenone | 3.5 | 1.5 | 6 |
| rose oxide, 1% | 1 | 1 | |
| rosalva | 0.5 | 0.5 | 1 |
| geranium Bourbon, natural or artificial | | 5 | 15 |
| essence of styrax | 3 | 2 | 3 |
| guaiacwood oil | 2 | | 10 |

TABLE 2

Formulas for Jasmin Bases, parts by wt.

| Ingredients | Perfume | Cream | Soap |
|---|---|---|---|
| benzyl acetate | 20 | 20 | 30 |
| benzyl alcohol | 10 | 14 | 10 |
| linalyl acetate | 15 | 15 | 15 |
| linalool | 5 | 8 | 10 |
| jasmone or isojasmone | 1 | 1 | 1 |
| peach aldehyde C-14 (undecalactone), 25% | 1 | 1 | 1 |
| hexylcinnamic aldehyde | 8 | 10 | 10 |
| indole, 10% | 8 | | 1.5 |
| methyl anthranilate | 1 | | |
| ylang-ylang oil extra | 10 | 10 | |
| ylang-ylang oil artificial for soaps | | | 10 |
| phenylethyl alcohol coeur | 20 | 20 | |
| phenylethyl alcohol white extra | | | 10 |
| jasmine absolute | 1 | | |
| methyl β-naphthyl ketone | | 1 | 1.5 |

TABLE 3

Composition of a Floral, Woody, Oriental Perfume Concentrate, parts by wt.

| Ingredients | Perfume | Cream | Soap |
|---|---|---|---|
| base for perfume | 40 | | |
| base for creams | | 40 | |
| base for soaps | | | 40 |
| aldehyde C-10 (decyl aldehyde), 1% | 5 | 5 | 5 |
| aldehyde C-11 (undecylenic aldehyde), 1% | 3 | 3 | 3 |
| methylnonylacetaldehyde, 10% | 1 | 1 | 1 |
| oil of tangerine | 2 | | |
| oil of bergamot natural | 6 | | |
| oil of bergamot artificial for soap | | | 6 |
| linalyl acetate | | 5 | |
| linalool | 2 | 3 | 2 |
| oil of neroli bigarade petals | 1 | | |
| oil of neroli artificial for creams and soaps | | 1 | 1 |
| dimethyl anthranilate, 10% | | 2 | 2 |
| oil of ylang-ylang extra | 5 | | |
| oil of ylang-ylang 2nd quality | | 5 | |
| oil of ylang-ylang for soaps | | | 5 |
| methylionone γ-coeur | 10 | | |
| methylionone γ-A | | 10 | 10 |
| synthetic rose | 12 | 12 | 12 |
| synthetic fasmin | 5 | 7 | 7 |
| oil of patchouli | 1 | 1 | 1 |
| tincture of natural musk (4 oz/gal) | 10 | | |
| tincture of civet (4 oz/gal) | 5 | | |
| Galaxolide (IFF), 50% | | 5 | 5 |
| jasmin absolute | 1 | | |
| rose absolute | 1 | | |

Perfumes are generally solutions of perfume concentrates or oils in alcohol. The strength of the solution of perfume oil in alcohol is about 10 to 25% or 12 to 32 oz per gal. The strength of the average successful perfume today is, in general, 15 to 20% or 18 to 24 oz per gal. For toilet waters and colognes the concentration of the fragrance component is much less, e.g. a typical formula for these products is about 3 grams of concentrate, 65 g. of 95% ethanol and 32 g. of dionized water.

All of the above described formulae are suitable for complexing with the present lactams and as complexes, have excellent hair and skin substantivity thus enabling them to be incorporated in many commerical formulations as exemplified in Table 4.

TABLE 4

Use Categories depilatories
special cleansers and detergents
permanent wave lotions
hormone creams and lotions
medicated creams and lotions
suntan lotions and oils
lotions
laundry rinses
creams
deodorants
hair rinses
miscellaneous hair treatment products
shampoos
makeup
face powders
lipsticks
colognes and perfumes
nail polish To form the fragrance complexes of the present invention, the osmophoric compound or fragrance formulation is mixed with the lactam in a weight ratio of between about 1:0.05 and about 1:10, preferably in a weight ratio of from about 1:0.2 to 1:6. The mixing is effected at a temperature at which the osmophoric component is liquid but non-volatile, e.g. a temperature within the range of between about 5° C. and 100° C. under about 10 to about 50 psig., more often between about 20° C. and about 80° C. under atmospheric pressure. The mixing operation is continued until a homogeneous solution is obtained, generally within a period of between about 5 minutes and about 2 hours, preferably between about 15 and 30 minutes. The pH during the mixing operation is most desirably maintained at about 7; although a pH of from about 5.5 to about 8 is also practicable.

The above mixing operation can be carried out in the presence or in the absence of an inert liquid diluent, most desirably an inert liquid having a pleasing odor such as an alcohol or an ester, e.g. isopropyl myristate, isopropyl palmitate, etc., of which ethanol and ethyl acetate are particularly recommended. The concentration of such diluted solutions, when employed, can vary between about 0.1 and about 15%; although solutions of from about 0.5 to about 5% are conveniently employed.

The concentration of the complexed osmophoric component in a cosmetic or industrial formulation is usually less concentrated than in a perfume. For example, the complexed fragrance can represent between about 0.1 and about 25 wt. %, preferably between about 0.75 and about 15 wt. %, of such commercial formulations. Somewhat higher concentrations can be used in industrial products to mask unpleasant odors. When the complex is synthesized in the presence of a diluent the product solution can be employed directly for addition into a commercial product; on the other hand, when the complexed fragrance is prepared in the absence of diluent, the complexed product is generally diluted to a concentration within the above range for ease of mixing and uniform distribution in the cosmetic or detergent formulation.

For the purposes of the present invention, a detergent formulation is intended to include a shampoo, a hair or skin conditioner, a liquid hard surface cleaner, a laundry detergent as well as a detergent rinsing solution.

Incorporation into a commercial formulation or cosmetic is carried out under the same conditions of mixing time, temperature and pressure as recited above for the formation of the complex. However, a buffer may be added to maintain the pH within a range of from about 5 to 8.5 during the blending operation. The present complexed fragrances are suitably employed as a component in any of the use categories outlined in Table 4, examples of which are as follows.

| A. Standard Dishwashing Composition | Vol. % |
|---|---|
| Water | 59.4 |
| Ethanol (95%) | 8.6 |
| Alfonic 1412-A 59.3% (ethylene oxide sulfate) | 20.0 |
| Alfonic 1412-10 (linear alcohol ethoxylate) | 1.1 |
| Sodium Chloride | .9 |
| Ethoxylated (9) nonyl-phenol (IGEPAL CA-630) | 7.5 |
| Fragrance | 2.5 |

| B. Machine Dishwashing Liquid | % by Wt. |
|---|---|
| Tetrasodium pyrophosphate | 22.0 |
| Sodium metasilicate | 10.00 |
| Sodium benzoate | 1.00 |
| Sodium xylene sulfonate (40%) | 1.00 |
| Glycol ether | 2.00 |
| Capryloamphocarboxy glycinate | 6.00 |
| 50/50 mixture of N-n-octyl- and N-n-dodecyl-2-pyrrolidones | 3.00 |
| Fragrance | 0.50 |
| $H_2O$ | 54.50 |

| C. Fine Fabric Washing Detergent | % by Wt. |
|---|---|
| Linear decyl benzene sulfonate | 5.00 |
| Coconut diethanolamide | 20.00 |
| Sodium lauryl ether sulfate (3 mol EO) | 15.00 |
| Sodium xylene sulfonate (40%) | 10.00 |
| Citric Acid | to pH 7 |
| Preservative | Q.S. |
| Colorant | Q.S. |
| N-n-dodecyl-2-pyrrolidone | 5.00 |
| Fragrance | 2.50 |
| Water | to 100% |

| D. Cold Water Phosphated Laundry Detergent | % by Wt. |
|---|---|
| Sodium tripolyphosphate | 48.0 |
| Sodium silicate (2:1 ratio) | 10.0 |
| Sodium sulfate | 17.5 |
| α-phosphono-w-(nonylphenoxy)-poly(oxy-1,2-ethanediyl) [GAFAC] | 17.5 |
| Fragrance | 2.0 |
| $H_2O$ | 5.0 |

| E. Sanitizing Detergent | % by Wt. |
|---|---|
| Magnesium aluminum silicate | 0.90 |
| Kelzan gum thickener | 0.45 |
| tetrasodium EDTA | 1.00 |
| Monazoline-O*/Imidazoline | 1.00 |
| Hydrochloric acid (37%) | 20.00 |
| Barquat MB-80 (alkyl dimethyl benzyl ammonium chloride) | 1.25 |
| 50/50 mixture of N-n-octyl- and N-n-dodecyl-2-pyrrolidones | 3.00 |
| Fragrance | 1.00 |
| $H_2O$ | 71.40 |

*substituted imidazoline of oleic acid

| F. Leather, Vinyl and Other Plastic Liquid Cleaner | % by Wt. |
|---|---|
| Ethoxylated alkylphenol | 10.00 |
| Arcosolve PM (propylene glycol methyl ether) | 5.00 |
| Isopropyl alcohol | 2.50 |
| Amyl acetate | 1.00 |
| 50/50 mixture of N-n-octyl- and N-n-dodecyl-2-pyrrolidones | 2.00 |
| Fragrance | 12.00 |
| Preservative | Q.S. |
| $H_2O$ | to 100% |

| G. Liquid Rug Shampoo | % by Wt. |
|---|---|
| Sipex 7WC concentrate (blend of ionic and nonionic surfactants, $C_{12}$ av. chain length) | 10.00 |
| Lauryl ether sulfate (3 mole EO) | 10.00 |
| Sodium tripolyphosphate | 2.00 |
| Ethyl carbitol solvent | 1.50 |
| Tinopal 5BM optical brightener | 0.05 |
| (diamino stilbene) | |
| N-n-dodecyl-2-pyrrolidone | 2.00 |
| Fragrance | 8.00 |
| Preservative | Q.S. |
| $H_2O$ | to 100% |

| H. Spray-Wipe Furniture Polish | % by Wt. |
|---|---|
| Petrolite C-36 emulsion* (20%) | 3.50 |
| Isopar E solvent ($C_8$–$C_9$ isoparaffin mixture of branched chain aliphatic hydrocarbons) | 32.50 |
| S-Maz 80 (Sorbitan monooleate) | 0.20 |
| Masil EM 1000 emulsion (dimethyl polysiloxane silcone emulsion, 60% active) | 3.40 |
| 50/50 mixture of N-n-octyl- and N-n-dodecyl-2-pyrrolidones | 3.00 |
| Fragrance | 0.40 |
| $H_2O$ | 57.00 |

*reacted microcrystalline wax, m.p. 195° F., needle penetration 77° F. is 7.5

| I. Toilet Bowl Cleaner | % by Wt. |
|---|---|
| Magnesium aluminum silicate | 0.90 |
| Xanthan gum thickener (Kelzan) | 0.45 |
| Tetrasodium EDTA | 1.00 |
| (Mona) Monazoline O Imidazoline | 1.00 |
| Hydrochloric acid (37%) | 20.00 |
| (Lonza) Barquat Mb-80 | 1.25 |
| n-Octyl pyrrolidone | 1.50 |
| n-Dodecyl pyrrolidone | 1.50 |
| Fragrance | 20.00 |
| Water | Q.S. |
| | 100.00 |

| J. Detergent Rinse Aid | % by Wt. |
|---|---|
| Nonoxynol 9 (9 av. ethoxylated nonyl phenol) | 30.00 |
| Isopropanol | 15.00 |
| Propylene glycol | 15.00 |
| N-n-octyl-2-pyrrolidone | 3.00 |
| Fragrance | 7.00 |
| $H_2O$ | 30.00 |

| K. Fabric Softener | % by Wt. |
|---|---|
| Miranol DM (monocarboxylic stearic derivative, sodium salt) | 3.00 |
| Arquad 2HT 75 (dimethyl[hydrogenated tallow] ammonium chloride) | 2.00 |
| N-n-dodecyl-2-pyrrolidone | 1.00 |
| Fragrance | 0.25 |
| $H_2O$ | 93.75 |

| L. Liquid Softening/Antistat Composition | % by Wt. |
|---|---|
| N-n-tetradecylpyrrolidone | 5.4 |
| (2) Igepal CO-660 | 23.0 |
| $H_2O$ | 55.7 |
| Ethanol | 15.0 |
| Fragrance | 0.9 |

(2) 100% active liquid/liquid condensation product of nonyl alcohol and ten units of ethylene oxide

| M. SKIN LOTION | |
|---|---|
| Ingredient | % by Wt. |
| Stearic Acid | 3.00 |
| Mineral Oil, 70 cts | 2.00 |
| Emulsifying Wax | 3.00 |
| Dimethicone | 1.50 |
| Deionized Water | QS |
| Carbomer 934* | 0.15 |
| Oleth-20** | 1.00 |
| N-decyl-2-pyrrolidone | 1.00 |
| Triethanolamine, 98% | 1.00 |
| Preservative | QS |
| Fragrance | 0.5 |

| N. FACIAL CREAM | |
|---|---|
| Ingredient | % by Wt. |
| Mineral Oil, 70 cts | 6.00 |
| Petrolatum | 4.00 |
| Lanolin | 3.00 |
| Glyceryl Monostearate, S.E. Acid Stable | 19.00 |
| Glycerine | 1.00 |
| N-octyl-2-pyrrolidone | 2.00 |

| -continued | |
|---|---|
| Deionized Water | QS |
| Preservative | QS |
| Fragrance | 0.1 |

*a crosslinked polymer of acrylic acid (B. F. Goodrich)
**the polyethylene glycol ether of oleyl alcohol (GAF Corp.)

O. SUNSCREEN LOTION

| Ingredient | % by Wt. |
|---|---|
| Myristyl Myristrate | 1.00 |
| PVP/Eicosene Copolymer | 2.00 |
| Glyceryl Stearate, S.E. | 3.50 |
| Dimethicone | 1.00 |
| N-dodecyl-2-pyrrolidone | 2.00 |
| Deionized water | Q.S. |
| Carbomer 940 | 0.10 |
| Triethanolamine | 0.10 |
| Preservative (Germaben II)* | Q.S. |
| Octyldimethyl p-aminobenzoic acid | 4.00 |
| Fragrance | 0.80 |

P. HAIR SHAMPOO

| Ingredient | % by Wt. |
|---|---|
| $C_{14}$-$C_{16}$ Alpha Olefin Sulfonate | 20.00 |
| Ammonium Lauryl Sulfate | 25.00 |
| Cocamidopropyl Betaine | 3.50 |
| N-dodecyl-2-pyrrolidone | 1.00 |
| Sodium Laureth-4-Phosphate | 1.00 |
| Hydrolyzed Animal Protein | 0.25 |
| Tetrasodium ethylene diamine tetra acetic acid | 0.15 |
| Deionized water | Q.S. |
| Fragrance | 2.5 |
| Preservative (Kathon CG)** | Q.S. |

*N-[1,3-bis(hydroxymethyl)-2,5-dioxo-4-imidazolidinyl-N,N'-bis(hydroxymethyl-)urea; Sutton Labs.
**5-chloro-2-methyl-4-isothiazolin-3-one (Rohm & Haas)

Q. BRUSHLESS SHAVING CREAM

| Ingredient | % by Wt. |
|---|---|
| a. | |
| Stearic Acid | 20.00 |
| Cetyl Alcohol | 1.00 |
| Lanolin | 2.00 |
| Isopropyl Palmitate | 6.00 |
| (Part a. added molten and mixed with Part b. at 80° C.) | |
| b. | |
| Hexylene Glycol | 8.00 |
| Triethanol Amine | 1.80 |
| Potassium Hydroxide | 0.50 |
| Borax | 2.00 |
| N-tetradecyl-2-pyrrolidone | 2.00 |
| Deionized water | Q.S. |
| Preservative (Kathon CG) | Q.S. |
| Fragrance | 3.00 |

R. AEROSOL SHAVING CREAM

| Ingredient | % by Wt. |
|---|---|
| Deionized Water | Q.S. |
| Glycerine | 5.8 |
| Oleth-20 | 1.0 |
| Butylated hydroxy anisole | 0.1 |
| Butylated hydroxy toluene | 0.1 |
| Stearic Acid | 7.5 |
| Lanolin | 0.5 |
| Mineral Oil, 70 cts | 2.4 |
| Cetyl Alcohol | 0.5 |
| Triethanolamine, 98% | 3.9 |
| Cocamide Diethanolamine | 0.5 |
| N-dodecyl-2-pyrrolidone | 2.0 |
| Fragrance | 0.5 |

Concentrate:Propellant Ratio - 95:5
Propellant:A-46 [80:20-Isobutane/Propane]

| S. Hand Lotion | Parts by Wt. |
|---|---|
| Water | 80 |
| Propylene glycol | 2 |
| Petrolatum | 3 |
| Stearic acid | 6 |
| Triethanolamine | 1 |
| Glycerin | 2 |
| N-dodecyl-2-pyrrolidone | 5 |
| Fragrance | 1 |

| -continued | |
|---|---|
| T. Waterless Hand Cleaner | % by Wt. |
| Deionized Kerosene | 44.00 |
| Stearic acid | 4.00 |
| Ethoxylated nonyl phenol | 4.00 |
| Propylene glycol | 4.00 |
| Arcosolve DPM (dipropylene glycol monomethyl ether) | 3.00 |
| Triethanolamine | 1.00 |
| N-n-octyl-2-pyrrolidone | 3.00 |
| Fragrance | 2.00 |
| Preservative | Q.S. |
| $H_2O$ | Up to 100% |

| U. Rug Shampoo | % by Wt. |
|---|---|
| Sodium lauryl sulfate | 12.00 |
| N-dodecyl-2-pyrrolidone | 3.00 |
| Sodium xylene sulfonate | 2.00 |
| Fragrance | 18.00 |
| $H_2O$ | to 100% |

In the above formulations A–U, the non-quaternized pyrrolidone components are replaced in whole or in part by the quaternized fragrance extenders of this invention.

Having generally described the invention, reference is now had to the following examples which provide preferred embodiments illustrating the invention but which are not to be construed as limiting to the scope thereof as more broadly defined above and in the appended claims.

EXAMPLE 1

Into a round bottom glass flask was introduced a 1:1 molar mixture of dimethyl-[(2-pyrrolidonyl)methyl] 3-octadecanamido propyl ammonium chloride and vanillin and the mixture heated to 80° C. with agitation until a homogeneous liquid was obtained (about 30 minutes). The melt was then allowed to cool to room temperature and the product was collected in quantitative yield as a viscous liquid.

EXAMPLE 2

Example 1 was repeated except that methyl-[(2-pyrrolidonyl)methyl]di-(3-octadecanamido propyl) ammonium chloride was employed as the complexing agent and the following composition was substituted as the fragrance component instead of vanillin.

| Osmophoric composition | WT. % |
|---|---|
| lilac extract | 8 |
| muguet | 5 |
| 3% musk extract | 5 |
| jasmine essence | 9 |
| tuberose absolute | 3 |
| 90% ethanol | 70 |

The pyrrolidonyl compound complexed with components of the jasmine essence, e.g. hexylcinnamic aldehyde and aldehyde C-14 to provide lasting fragrance.

EXAMPLE 3

The product of Example 1 (1.0 g.) was dissolved in ethanol at room temperature to provide a 1% alcoholic solution. About 5 g. of the complex in solution was then mixed at room temperature into a conditioning shampoo having the following formulation:

| INGREDIENT | % BY WEIGHT |
| --- | --- |
| Deionized water | 52.65 |
| Sodium lauryl sulfate | 40.00 |
| Cocamide DEA | 2.50 |
| Cocamido propyl betaine | 3.50 |
| Sodium laureth 4-phosphate | 0.80 |
| Tetrasodium EDTA | 0.20 |
| Hydrolized silk protein | 0.25 |
| Methyl chloroisothiazolinone and methyl isothiazolinone | 0.10 |
| | 100.00 |

The complexed fragrance was mixed in the formulation at room temperature for about 5 minutes and then bottled for future use.

The above procedure was repeated except that, instead of the complex, 0.05 g. of vanillin in ethanol was added to the identified shampoo formulation.

After 14 days, the above formulations were used as a shampoo on two test subjects. The hair of both subjects was set and dried under similar conditions.

The formulation containing the complex retained the fragrance 24 hours longer than that which contained non-complexed vanillin fragrance. This extension of scent emanation was due to the skin and hair substantivity of the complexed form of the fragrance.

EXAMPLE 4

The product of Example 1 was dissolved in ethanol at room temperature to provide a 5% solution in alcohol. About 2.5 g. of the complex in solution was then added and mixed at room temperature into a standard roll-on antiperspirant having the following formulation.

| Ingredients | % by Wt. |
| --- | --- |
| deionized water | 50.00 |
| glyceryl monostearate (self emulsifying-acid stable) | 4.00 |
| isopropyl palmitate | 6.50 |
| ceteareth-55 (polyethylene glycol ether of cetearyl alcohol) | 1.00 |
| chlorhydrol (antiperspirant 50% soln.) | 38.50 |
| | 100.00 |

After a uniform mixture was obtained the solution was packaged in a roll-on dispenser. The above procedure then was repeated to provide 5 separate samples of antiperspirant containing the complex in roll-on dispensers.

The entire procedure described above was repeated, except that 2.5 g of non-complexed vanillin was substituted for the product of Example 1.

Ten volunteer female subjects were tested with the above samples, 5 with the antiperspirant containing the 1:1 complexed fragrance and 5 with the uncomplexed fragrance. It was found that the fragrance persisted for 18 hours with no noticeable perspiration odor on the subjects tested with the formulation containing the complexed fragrance; whereas, after 4 hours the fragrance had dispersed and a faint perspiration odor was detected after 5 hours on the subjected tested with the non-complexed fragrance formulation.

EXAMPLE 5

The above procedure in Example 4 is repeated except that an antiperspirant stick formulation having the following composition is substituted for the roll-on solution.

| Ingredient | % by Weight |
| --- | --- |
| aluminum zirconium tetrachlorohydrex GL 4 (REZAL 36GP) | 20.50 |
| Stearyl alcohol | 22.00 |
| Glyceryl monostearate (acid stable/self emulsifying) | 1.00 |
| Talc, 325 mesh | 1.00 |
| Carbowax 1000 (polyethylene glycol) | 5.00 |
| Cab-O-Sil-M-5-Silica* | 1.50 |
| Siloxane F-22 | 49.00 |
| | 100.00 |

*Fumed Silica

In the present case the complexed and non-complexed fragrances were incorporated by melting the above formulation, mixing in the osmophoric component until a uniform distribution was obtained, allowing the resulting composition to cool to room temperature and then recovering. The product as a soft waxy substance. Ten male subjects were tested by rubbing on the soft stick antiperspirant. The fragrance emission on the five subjects tested with the composition containing the complexed fragrance stick deodorant lasted for 12 hours without any trace of perspiration odor. On the five subjects tested with the non-complexed fragrance stick deodorant the vanillin scent lasted only 4 hours, after which there was a noticeable odor of perspiration.

EXAMPLE 6

The product of Example 1 was dissolved in ethanol at room temperature to provide a 1% solution in alcohol. About 4 g. of the complex in solution was then added and mixed at room temperature into a standard pet shampoo having the following formulation.

| Ingredient | % By Weight |
| --- | --- |
| magnesium aluminum silicate (veegum, reg.) | 1.00 |
| deionized water | 41.30 |
| sodium cocoyl isethionate, 83% | 19.00 |
| sodium methyl cocoyl taurate, 24% | 26.00 |
| cetyl alcohol | 1.80 |
| glyceryl monostearate, acid stable | 5.90 |
| laneth - 10 acetate (polyethylene glycol ether of lanolin alcohol) | 3.50 |
| synergized pyrethrins (50% piperonyl butoxide and 10% pyrethrins) | 0.50 |
| captan (vancide 89 RE) | 1.00 |
| | 100.00 |

Five portions of pet shampoo were prepared as above and tested on 5 canines. After drying, the fur of the animals had a soft, silky appearance and, after 2 days the pleasing vanillin scent still adhered to the fur.

After 1 month, the above experiment was repeated except that 4 g. of non-complexed vanillin was added to the above pet shampoo formulation. The same canines were shampooed with the non-complexed fragrance composition. After drying, the fur, while soft, had noticeably less luster and the pleasing vanillin scent on the fur endured for only 12 hours. The improved results achieved with the present complexed fragrance is due to the high skin and hair substantivity of the complex and to the complexed form of the fragrance.

EXAMPLE 7

A. Preparation of dimethyloctadecyl[(2-pyrrolidonyl) methyl]ammonium tosylate ($SO_3$-$C_6H_4$-$CH_3$)

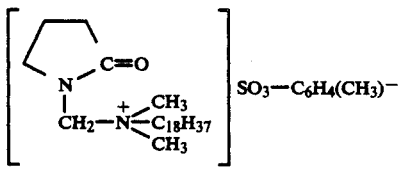

by solubility exchange of quaternaries.

To a flask equipped with stirrer and thermometer was added at ambient temperature 50.0 g. distilled water 7.2 g. sodium hydroxide solution (50%) and 13.3 g. (0.069 m) p-toluenesulfonic acid monohydrate, [$C_6H_4(CH_3)SO_3H$]. The mixture was stirred at ambient temperature for about 0.5 hour, after which 30.0 g. (0.069 m) dimethyloctadecyl[(2-pyrrolidonyl) methyl] ammonium chloride was added. The reaction mixture was heated to 40°–45° to ensure complete solution and stirring continued for an additional 2 hours. The reaction was then cooled to 10°–15° C. to precipitate the crude tosylate salt product. The crude product was filtered to recover 19.8 g. of white solid product, which product was found to have 98.2% quaternized product, 0.4% amine, and 0.04% chloride. The quaternized product of this example can be employed as a complexing agent in the composition shown in Example 2.

B. Preparation of dimethyl-octadecyl[(2-pyrrolidonyl) methyl] ammonium tosylate by Ion Exchange Resin To a glass chromatography column was charged 450 g. Amberlyte IRA 900 ion exchange resin*. The column was washed with one liter of methanol followed by one liter of distilled water.

* a macroreticular strongly anion exchange resin having a halide attached to the resin matrix of styrene/divinylbenzene A solution of sodium tosylate, prepared by addition of 332.9 g. p-toluenesulfonic acid monohydrate to 1720 g. water followed by neutralization with 140 g. of 50% sodium hydroxide, was then passed through the packed column at a rate sufficient to permit displacement of the Amberlyte halide and to replace it with toluene sulfonate. The column was then washed with one 1 liter of methanol. A solution of 153 g. dimethyloctadecyl[2pyrrolidonyl) methyl] ammonium chloride (98.4% pure) in 500 ml methanol was passed through at a rate sufficient to exchange the chloride of the lactam with the toluene sulfonate of the resin. The column was then washed with 500 ml methanol and the methanol evaporated leaving 200 g. of 98% pure quaternized product.

EXAMPLE 8

Example 7B was repeated except that sodium methyl sulfonate was substituted for sodium toluene sulfonate. The resulting quaternized product, dimethyloctadecyl N-[(2-pyrrolidonyl)methyl] ammonium methylsulfonate, (94.3% pure quaternized compound) was recovered. The quaternized product of this example can be employed as a complexing agent in the composition shown in Example 2.

EXAMPLE 9

The same result as reported in Example 8 was achieved when sodium methosulfate was substituted for sodium toluene sulfonate. The quaternized product of this example can be employed as a complexing agent in the composition shown in Example 2.

EXAMPLE 10

A. Into a round bottom glass flask was introduced a 5:1 molar mixture of dimethyldodecyl-[(2-pyrrolidonyl) methyl] ammonium tosylate and vanillin and the mixture heated to 80° C. with agitation until a homogeneous liquid was obtained (about 30 minutes). The melt was then allowed to cool to room temperature and the product was collected in quantitative yield as a viscous liquid. This product was diluted to a 5% solution with 24 parts 9 moles ethoxylated nonyl phenol, 15 parts ethanol, 55 parts water and 1 part cationic surfactant.

Ten cotton terry cloth towels were mechanically washed for 10 minutes with concentrated ALL (0.20% use level) detergent and then subject to a first rinse cycle for 2 minutes. The towels were drained to dampness by a 1 minute centrifuge cycle and then subjected to a second rinse at 45° C. At the beginning of the second rinse, 6.2 g. of the complexed vanillin, prepared as above was added to the rinse water to provide a rinse containing 0.03% of the complex. The towels were agitated in the second rinse for 3 minutes after which they were drained to dampness as above and dried in a mechanical dryer.

B. The entire procedure above was repeated except that 1 g. of non-complexed vanillin was similarly diluted and added to the second rinse water instead of the complexed vanillin.

The dried towels recovered from part A. were soft and pliable and retained the pleasing scent of vanillin for 4 days; whereas those recovered from part B. were somewhat stiffer and retained the vanillin scent for only 12 hours.

Experiment A is repeated 4 times except that the dimethyl-[(2-pyrrolidonyl)methyl] dodecyl ammonium tosylate is replaced with each of the following compounds 1-4.

1. dimethyl-[(2-pyrrolidonyl)methyl] heptadecylamido propyl ammonium tosylate, i.e.

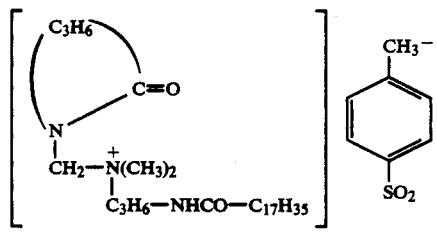

2. dimethyl-[(2-pyrrolidonyl)methyl]3-pentadecylamidopropyl ammonium tosylate
3. dimethyl-[(2-pyrrolidonyl)methyl]3-eicosylamidopropyl ammonium tosylate, and
4. methyl-[(2-pyrrolidonyl)methyl](3-decylamidopropyl) 3-methylamidopropyl ammonium methyl sulfate, i.e.

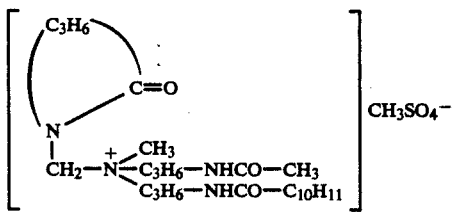

The results with these compounds are substantially the same as those described above for the lactam of part A.

It will be understood that any of the afore-designated quaternary lactams can be substituted in the examples for complexing with the indicated fragrances or fragrance compositions and that any of the described fragrances or fragrance compositions can also be substituted in the examples to provide complexes with said quaternary lactams and to provide products having improved skin and hair substantivity and extended scent emanation. Also any of the formulations A-U can be substituted in the examples for incorporation of the complexed fragrances of this invention to provide improved formulations having extended odoriferous emanation.

What is claimed is:

1. The composition comprising a quaternary lactam having the formula:

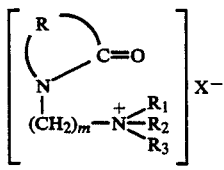

wherein $X^-$ in an anion; m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxyalkyl, alkoxy, alkyleneoxyalkenyl, alkylhydroxy, aryl, aralkenyl, aralkyl, alkaryl,

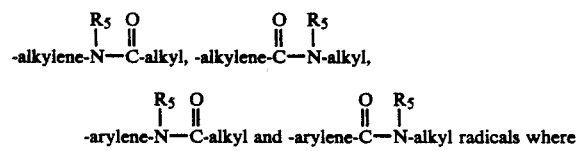

-alkylene-N—C-alkyl, -alkylene-C—N-alkyl,

-arylene-N—C-alkyl and -arylene-C—N-alkyl radicals where $R_5$ is hydrogen or alkyl, said groups each having up to 30 carbon atoms and at least one of $R_1$, $R_2$ and $R_3$ is a radical having from 8 to 30 carbon atoms, except that alternatively $R_2$ and $R_3$ with the quaternized nitrogen can form a 5 to 14 membered heterocyclic ring having from 1 to 2 heteroatoms selected from the group of oxygen, nitrogen and sulfur, in which case $R_1$ can be any of the aforementioned groups or can represent a bond in an unsaturated quaternized heterocyclic ring; and an odoriferous fragrance containing compound having an acidic hydrogen atom and from 3 to 50 carbon atoms wherein the weight ratio of fragrance to quaternary lactam is between about 1:0.05 and about 1:10.

2. The composition of claim 1 wherein said odoriferous compound is a normally volatile compound and is selected from the group consisting of a hydroxylated compound, an aldehyde, a primary or secondary amine, a primary or secondary amide, a carboxylic compound, an essential perfume oil and mixtures thereof.

3. The composition of claim 1 wherein said odoriferous compound is a hydroxylated compound.

4. The composition of claim 3 wherein said hydroxylated compound is vanillin.

5. The composition of claim 1 wherein $X^-$ is an organic anion.

6. The composition of claim 5 wherein $X^-$ is tosylate.

7. The composition of claim 5 wherein $X^-$ is methyl sulfonate.

8. The composition of claim 5 wherein $X^-$ is methyl sulfate.

9. The composition of claim 5 wherein $X^-$ is ethyl sulfate.

10. The composition of claim 1 wherein the quaternary lactam has the formula

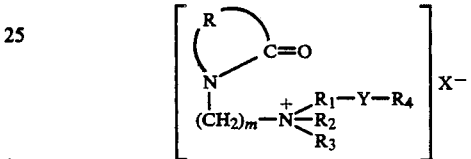

wherein m is an integer having a value of from 1 to 4; R is alkylene containing from 3 to 8 carbon atoms and is optionally substituted with lower alkyl; $R_1$ is alkylene containing from 1 to 4 carbon atoms, phenylene or naphthylene optionally substituted with lower alkyl;

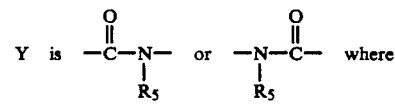

$R_5$ is hydrogen or lower alkyl; $R_4$ is alkyl having from 1 to 30 carbon atoms; $R_2$ and $R_3$ are each independently selected from the group of —$R_1$—Y—$R_4$, alkyl, alkyleneoxyalkyl, alkylhydroxy, aryl, aralkyl, aralkenyl, alkenylaryl and alkaryl said groups each having up to 30 carbon atoms and at least one of $R_4$, $R_2$ and $R_3$ having 8 or more carbon atoms and $X^-$ is an anion.

11. The composition of claim 1 wherein the quaternary lactam has the formula

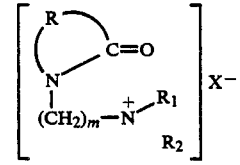

wherein $X^-$ is an anion; m is an integer having a value of from 1 to 4; R is linear alkylene having from 3 to 8 carbon atoms and is optionally substituted with $C_1$ to $C_4$ alkyl; $R_1$ forms a double bond in the heterocyclic ring with the quaternized nitrogen or is selected from the group consisting of alkyl, hydroxyalkyl, alkyleneoxyalkyl, alkyleneoxyalkenyl, aryl, alkaryl, aralkyl, aralkenyl, alkyleneamidoalkyl, alkylenecarbamoylalkyl, arylcarbamoylalkyl and arylamidoalkyl and $R_2$, together with the quaternary nitrogen atom forms a 5 to 14 membered heterocyclic structure containing up to 2 hetero atoms, selected from the group of nitrogen, oxygen and sulfur.

12. The composition of claim 1 wherein the quaternary lactam has the formula

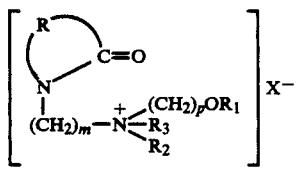

wherein $X^-$ is an anion, m and p are each integers having a value of up to 4; R is linear $C_3$ to $C_8$ alkylene in which alkylene may be substituted with lower alkyl; $R_1$ is alkyl or alkenyl having from 1 to 30 carbon atoms and $R_2$ and $R_3$ are each independently selected from the group consisting of —$(CH_2)_pOR_1$, alkyl, hydroxyalkyl, aryl, alkaryl, aralkyl, aralkenyl, alkylene amidoalkyl, arylamidoalkyl, alkylenecarbamoylalkyl and arylcarbamoylalkyl radicals, said groups having up to 30 carbon atoms and at least one of $R_1$, $R_2$ and $R_3$ is a radical containing from 8 to 30 carbon atoms.

13. The process which comprises intimately mixing an odoriferous fragrance bearing component containing a compound having an acidic hydrogen atom and from 3 to 50 carbon atoms and an effective fragrance extending amount of a quaternary lactam of claim 1 at a temperature and pressure at which said components are in the liquid state.

14. The process of claim 13 wherein the odoriferous fragrance bearing component is mixed with said quaternary lactam in a weight ratio of between about 1:0.05 and about 1:10 to produce a complexed product.

15. The process of claim 14 wherein said weight ratio is between about 1:0.2 and about 1:6.

16. The process of claim 13 wherein said odoriferous compound is a hydroxylated compound.

17. The process of claim 16 wherein said odoriferous compound is vanillin.

18. The process of adding an effective fragrance producing amount of the composition of claim 1 to a nonfragrant formulation.

19. The process of adding between about 0.1 and about 25 wt. % of the composition of claim 1 to a cosmetic formulation.

20. The process of adding between about 0.1 and about 25 wt. % of the composition of claim 1 to ethanol.

21. The process of adding between about 0.1 and about 25 wt. % of the composition of claim 1 to a detergent formulation.

22. The process of adding between about 0.1 and about 25 wt. % of the composition of claim 1 to a perfume base formulation.

23. The process of adding between about 0.1 and about 25 wt. % of the composition of claim 1 to a cologne base formulation.

* * * * *

UNITED STATES PATENT OFFICE
CERTIFICATE OF CORRECTION

Patent No. 4,952,559      Dated August 28, 1990

Inventor(s) RATAN K. CHAUDHURI, DAVID J. TRACY, ROBERT B. LOGIN AND MICHAEL W. HELIOFF It is certified that error appears in the above-identified patent and that said Letters Patent is hereby corrected as shown below:

The inventors listed in [75] following the Title [54] should read: RATAN K. CHAUDHURI, Butler; DAVID J. TRACY, Lincoln Park; ROBERT B. LOGIN, Oakland; MICHAEL W. HELIOFF, Westfield, all of N.J.

Signed and Sealed this

Twelfth Day of November, 1991

Attest:

HARRY F. MANBECK, JR.

Attesting Officer      Commissioner of Patents and Trademarks